(12) United States Patent
Dias et al.

(10) Patent No.: US 7,494,339 B2
(45) Date of Patent: Feb. 24, 2009

(54) COMPOSITIONS FOR USE AS DENTAL CROWNS AND METHODS FOR PREPARING DENTAL CROWNS

(75) Inventors: Walter R. Dias, Milford, DE (US); Fuming Sun, Middletown, DE (US); Robert V. Hare, Georgetown, DE (US)

(73) Assignee: Dentsply International, Inc., York, PA (US)

( * ) Notice: Subject to any disclaimer, the term of this patent is extended or adjusted under 35 U.S.C. 154(b) by 0 days.

(21) Appl. No.: 11/502,139

(22) Filed: Aug. 10, 2006

(65) Prior Publication Data

US 2007/0148623 A1 Jun. 28, 2007

Related U.S. Application Data

(60) Provisional application No. 60/706,882, filed on Aug. 10, 2005.

(51) Int. Cl.
*A61C 5/10* (2006.01)
(52) U.S. Cl. .................... 433/223; 433/222.1
(58) Field of Classification Search ................ 433/223, 433/218, 202.1, 222.1, 212.1, 167; 264/19–20; 523/115, 116; 106/35
See application file for complete search history.

(56) References Cited

U.S. PATENT DOCUMENTS

| | | | |
|---|---|---|---|
| 3,949,477 A | 4/1976 | Cohen et al. | |
| 4,449,928 A | 5/1984 | von Weissenfluh | |
| 4,571,188 A | 2/1986 | Hamilton | |
| 4,600,389 A * | 7/1986 | Schwartz | 433/217.1 |
| 4,695,254 A * | 9/1987 | Herrell | 433/213 |
| 4,721,735 A | 1/1988 | Bennett et al. | |
| 4,872,936 A * | 10/1989 | Engelbrecht | 156/307.3 |
| 4,902,232 A * | 2/1990 | Neustadter | 434/263 |
| 5,370,221 A * | 12/1994 | Magnusson et al. | 206/221 |
| 5,376,691 A | 12/1994 | May et al. | |
| 5,554,665 A * | 9/1996 | Tateosian et al. | 522/30 |
| 5,709,548 A * | 1/1998 | Oxman et al. | 433/218 |
| 5,807,101 A | 9/1998 | Scalzo | |
| 5,944,527 A * | 8/1999 | Hasel | 433/212.1 |
| 5,977,199 A * | 11/1999 | Xie | 522/8 |
| 6,043,296 A * | 3/2000 | Davies et al. | 523/116 |
| 6,057,383 A | 5/2000 | Volkel et al. | |
| 6,133,339 A * | 10/2000 | Xie et al. | 523/116 |
| 6,220,858 B1 | 4/2001 | McKenna et al. | |
| 6,306,206 B1 * | 10/2001 | Fischer et al. | 106/35 |
| 6,386,865 B1 | 5/2002 | Suh et al. | |
| 6,437,019 B1 * | 8/2002 | Rusin et al. | 523/117 |
| 6,592,369 B2 * | 7/2003 | Sun et al. | 433/167 |
| 6,799,969 B2 | 10/2004 | Sun et al. | |
| 6,843,951 B2 | 1/2005 | Vogel et al. | |
| 6,884,073 B2 * | 4/2005 | Chilibeck | 433/219 |
| 7,094,057 B2 | 8/2006 | Friedman | |
| 7,141,616 B2 * | 11/2006 | Hecht et al. | 523/115 |
| 2003/0008967 A1 * | 1/2003 | Hecht et al. | 524/507 |
| 2003/0134932 A1 | 7/2003 | Lehmann et al. | |
| 2003/0134933 A1 * | 7/2003 | Jin et al. | 523/115 |
| 2003/0166740 A1 * | 9/2003 | Mitra et al. | 523/115 |
| 2004/0086830 A1 * | 5/2004 | Allred | 433/89 |
| 2004/0166740 A1 | 8/2004 | Jorgensen | |
| 2006/0115793 A1 * | 6/2006 | Kopelman et al. | 433/215 |
| 2007/0072146 A1 * | 3/2007 | Pierson | 433/90 |
| 2007/0088097 A1 * | 4/2007 | Qian | 523/115 |

FOREIGN PATENT DOCUMENTS

| | | |
|---|---|---|
| EP | 0 166 009 | 6/1984 |
| EP | 1 245 219 | 9/2005 |

OTHER PUBLICATIONS

Dr. Gregori M. Kurtzman, Fabricating Temporaries Using TempSpan Dual-Cure Resin, Dental Products Report, Aug. 2005.
Livaditis et al., "Crown Foundations With A Custom Matrix, Composites, and Reverse Carving," Journal Of Prosthetic Dentistry, May, 1997.
PCT International Search Report for PCT International Application No. PCT/US2006/031200, Apr. 12, 2007.

* cited by examiner

*Primary Examiner*—Ralph A Lewis
*Assistant Examiner*—Sunil K Singh
(74) *Attorney, Agent, or Firm*—Douglas J. Hura; Daniel W. Sullivan

(57) ABSTRACT

The invention provides a method of forming dental restorations, particularly dental crowns. The method involves applying a flexible cement composition to a prepared tooth surface. The composition is polymerized so that it substantially hardens. A composite crown-forming material is dispensed into a substantially transparent plastic matrix. The matrix is placed in the mouth of the patient so that the composite material is molded over the tooth surface. Then, the material is irradiated with curing light, through the matrix, so that it hardens to form a dental crown. The crown has good mechanical strength and is resistant to fracturing and breaking.

8 Claims, No Drawings

COMPOSITIONS FOR USE AS DENTAL CROWNS AND METHODS FOR PREPARING DENTAL CROWNS

CROSS-REFERENCE TO RELATED APPLICATIONS

This application claims the benefit of U.S. Provisional Patent Application 60/706,882 having a filing date of Aug. 10, 2005, the entire contents of which are hereby incorporated by reference.

BACKGROUND OF THE INVENTION

1. Field of the Invention

The present invention relates generally to methods for preparing artificial dental crowns, bridges, and other restorations. The invention also encompasses compositions used in such methods.

2. Brief Description of the Related Art

A dental professional prepares an artificial crown to cover a tooth for many different reasons. In general, the crown is used to restore the anatomy, function, and aesthetics of part or all of the coronal portion of the natural tooth. For example, the crown may be needed to: 1) protect a weak tooth from breaking (the tooth may be weak as a result of decay or other disease); 2) hold together parts of a cracked tooth; 3) restore a tooth that is already broken or severely worn down; 4) cover and support a tooth with a large filling; 5) hold a dental bridge in place; 6) cover misshaped or severely discolored teeth; or 7) cover a dental implant.

In a conventional procedure for preparing a dental crown, the patient must make multiple visits to the dentist. In the first visit, the dentist examines and prepares the tooth that will receive the crown. First, the dentist may take an impression of the patient's dental anatomy including the tooth that will ultimately receive the crown. To make the impression, the dentist commonly uses a dispensing syringe to inject a paste-like material into an impression tray. Then, the dentist inserts the filled tray into the patient's mouth, and the patient bites down on the paste in the tray to form the impression. After the dentist has taken the impression, the patient is anesthetized, and the tooth, which will receive the crown, is prepared. First, the dentist may remove any dental caries from the tooth using a dental bur or other instrument. Then, the dentist performs "crown prep" work on the tooth by filing and grinding it to a "core" or "stump". A high-speed or low-speed handpiece, which is equipped with a diamond bur, is used typically to grind the tooth and prepare the core. Next, the dentist takes a final impression of the prepared tooth.

In order that a more accurate impression can be made, the dentist may first use a gingival retraction device to retract the gingival tissue around the tooth that will receive the crown. Dentists commonly use gingival retraction cord, which is pressed into the gingival sulcus around the prepared tooth, with a hand instrument. As the gingival tissue is retracted, the margins of the prepared tooth are exposed. The dentist thus can take a more accurate and detailed impression. The impression of the prepared tooth is made using a paste-like material in the same manner as discussed above. After taking the impression of the prepared tooth, the dentist sends the impression to a dental laboratory, which makes the permanent crown.

During the first office visit, the dentist places a temporary crown on the prepared tooth to cover and protect the tooth, while the permanent crown is being fabricated. The temporary crown is made from a polymeric paste-like material such as an acrylic. More particularly, a polymerizable material, which is prepared from base and catalyst pastes, may be used to form the temporary crown. The base and catalyst pastes may be dispensed from a double-barrel syringe having a dispensing tip with a static mixer. The base and catalysts pastes are extruded through the static mixer and directly onto a pre-made impression or plastic matrix. Then, the impression or matrix containing the polymerizable (mixed base and catalyst) material is inserted into the patient's mouth. The dentist presses on the impression or matrix so that the polymerizable material is molded over the prepared tooth. Then, the impression or matrix containing the molded, partially-cured material is removed from the patient's mouth. The polymerizable material is fully cured by chemical-curing, light-curing, heat-curing, or other suitable process, and the temporary crown is formed. The temporary crown is then cemented to the tooth using a temporary dental cement.

Various temporary crown and bridge materials are available from companies that supply dental products. For example, Integrity™ A2 (Dentsply International) is a temporary crown and bridge material that is made from base and catalyst pastes mixed together in a 10:1 (base/catalyst) volume ratio. Protemp™ 3 Garant™ A2 (3M ESPE) is another temporary crown and bridge material that mixes base and catalyst pastes in a 10:1 volume ratio. Structur™ 2 SC A3 (Voco) and Temphase™ (Kerr) are commercially available cartridges that mix the base and catalyst pastes in a 1:1 volume ratio.

Compositions that can be used to make temporary crown and bridges are described generally in the patent literature. For example, May et al., U.S. Pat. No. 5,376,691 discloses dental cement for making temporary crowns and bridges. The dental cement is prepared from a first paste comprising a difunctional acrylate such as urethane diacrylate, an activator such as a tertiary amine, and a radiopaque filler such as barium and/or strontium glasses. The second paste includes no substances having active double bonds, a catalyst such as dibenzoyl peroxide, a silicon dioxide material, and a softener that cannot be polymerized along with the other components but is sufficiently insoluble in the mouth. The softeners can be selected from such compounds as liquid paraffins, long-chain glycols, and inert alkylphthalates.

Tateosian et al., U.S. Pat. No. 5,554,665 discloses a dental composition that is formed by the static mixing of two complementary pastes. A catalyst paste includes a polymerizable methacrylate, a peroxide, and a stabilizer such as butylated hydroxytoluene. The stabilizer is effective at preventing polymerization for at least 180 days at 23° C. A complementary accelerator and radiation-cure initiator paste includes a polymerizable methacrylate and a reducing agent for the peroxide such as dihydroxyethyl-p-toluidine. According to the '665 patent, the paste compositions preferably have substantially the same viscosity and are mixed in a volume ratio between 1:1 and 1:5.

Xie, U.S. Pat. No. 5,977,199 discloses a delivery system for delivering dental cement material for making temporary crowns and bridges. A catalyst paste and base paste are dispensed from a dual cartridge and mixed in a static mixer to form a polymerizing material. The catalyst paste comprises at least one polymerizable monomer, polymerization initiator, polymerization inhibitor, and filler. The base paste comprises at least one polymerizable monomer, at least one polymerization accelerator, polymerization inhibitor, and filler. According to the '199 patent, the viscosity of the catalyst paste must be substantially greater than the viscosity of the base paste in order for the mixture to cure effectively.

At the second office visit, the dentist removes the temporary crown. The dentist cleans the tooth, removing any residual temporary cement. The dentist further checks the color and occlusal fit of the permanent crown. If satisfactory, the dentist anesthetizes the tooth and then affixes the permanent crown to the tooth using permanent cement.

As described above, in a traditional crown preparation, fitting, and mounting procedure, the patient must make multiple visits to the dentist. Furthermore, the procedure involves the preparation of temporary or provisional crowns, which can be time-consuming and costly. The patient and dentist may feel added stress and anxiety due to the many anesthetization and fitting steps involved in this conventional process. It thus would be desirable to develop a method, whereby a dentist could prepare a permanent dental crown for a patient in a single office visit. Ideally, the dentist would be able to design and fabricate the crown "chair-side" and mount the crown on the patient's tooth in a single office visit. The crown should be made from a material having good aesthetics so that the crown matches the shade of the natural teeth. The crown should further have good mechanical strength and integrity so that the crown will not break or fracture easily.

The present invention provides such a method for making dental crowns and compositions that can be used to make such crowns. The method is efficient and allows the dentist to provide a crown that is aesthetically-pleasing and has good mechanical strength as well as other beneficial features and advantages.

SUMMARY OF THE INVENTION

The present invention relates to new methods for making dental crowns, bridges, or other restorations. The invention also includes compositions that can be used to make such crowns, bridges, and restorations.

In one embodiment of this invention, a polymerizable flexible cement composition is provided. The cement composition is applied to a prepared tooth surface, which will receive the crown, and the composition is polymerized so that it substantially hardens. Then, a composite crown-forming material is dispensed into a substantially transparent plastic matrix. The composite material includes a polymerization system capable of being activated by light. The plastic matrix containing the composite material is placed in the mouth of the patient so that the material is molded over the prepared tooth surface. The composite material is applied over the layer of hardened, but flexible, cement. The composite material is irradiated with light so that the material hardens to form a crown. Then, the hardened crown is removed from the surface of the tooth. The crown may be trimmed and polished as needed. A sealant may be applied to the crown to provide a glossy surface finish. Then, the crown may be permanently affixed to the tooth using dental cement.

DETAILED DESCRIPTION OF THE PREFERRED EMBODIMENTS

The present invention relates to a method of forming dental restorations, particularly a dental crown. In accordance with this invention, the dentist may use a light-curing dental composition to fabricate and mount the dental crown during a single office visit. Although the method of this invention is described primarily herein as being suitable for making a dental crown, it should be recognized that this method can be used to make other restorations such as dental bridges.

In accordance with this method, a dentist first takes a pre-operative impression or matrix of the patient's teeth including the tooth that will receive the crown. The dentist preferably uses a transparent plastic matrix, which is made of silicone, in order to take the impression of the teeth. It is important that the matrix be transparent, because curing light is transmitted through the matrix in a subsequent step of the process as discussed in further detail below. The dentist presses the silicone matrix on the surface of the teeth to form the impression. After the impression has been formed in the silicone matrix, the dentist removes the matrix from the teeth. The resulting impression is an accurate negative likeness of the anatomy of the teeth, particularly the occlusal surface of the teeth.

Next, the tooth, which will receive the crown, is prepared using conventional techniques. This "crown prep" work typically involves filing and grinding the tooth to a "core" or "stump." The dentist may use a high-speed or low-speed handpiece, which is equipped with a diamond bur, to grind the tooth and prepare the core.

The dentist then applies a thin layer of "spacer material" to the prepared tooth. The spacer material is applied over the surface of the prepared tooth, but it is not applied at the margins of the tooth. The spacer material is preferably a flexible cement composition. In one embodiment of this invention, the spacer material is made from a catalyst paste and base paste as described further below. It should be understood that the following composition is provided for illustration purposes only and represents only one embodiment of a composition that can be used in accordance with this invention.

Catalyst Paste for Spacer Material (Flexible Cement)

The spacer material (flexible cement) may be prepared from a catalyst paste and a base paste. Conventional auto-mix systems, such as double barrel syringes, can be used to mix the catalyst and base components and dispense the resulting spacer material. The catalyst and base pastes are stored in separate cartridges and dispensed from the cartridges in a pre-determined volume ratio to form a mixed composition.

Preferably, the catalyst paste, which is mixed with the base paste to form the spacer material composition, comprises a polymerizable monomer, a polymerization initiator, a polymerization inhibitor, and filler.

Suitable polymerizable monomers for use in the catalyst paste include, for example, acrylate resins, methacrylate resins, or mixtures thereof. For example, polymerizable monomers such as ethylene glycol di(meth)acrylate, diethylene glycol di(meth)acrylate, triethylene glycol di(meth)acrylate, tetraethylene glycol di(meth)acrylate, neopentyl glycol di(meth)acrylate, 1,4-butanediol di(meth)acrylate, 1,6-hexanediol di(meth)acrylate, trimethylolpropane tri(meth)acrylate, 2,2-bis[4-(2-hydroxy-3-acryloyloxypropoxy)phenyl]propane, 2,2-bis[4-(2-hydroxy-3-methacryloyloxypropoxy)phenyl]propane (Bis-GMA), 2,2-bis[4-(acryloyloxy-ethoxy)phenyl]propane, 2,2-bis[4-(methacryloyloxy-ethoxy)phenyl]propane, Urethane di(meth)acrylate (UDMA), alkoxylated pentacrythritol tetraacrylate, ethoxylated bisphenol A dimethacrylate, dipentaerythritol pentacrylate phosphoric acid ester (PENTA), bis[2-(methacryloxyloxy)-ethyl]phosphate, and the like can be used.

The polymerization initiator used in the catalyst paste can be chosen from known polymerization initiators such as, for example, organic peroxides including dibenzoyl peroxide (BPO), di-p-chlorobenzoyl peroxide, di-2,4-dichlorobenzoyl peroxide, tertiary butyl peroxybenzoate, methyl ethyl ketone peroxide, ditertiary butyl peroxide, dicumyl peroxide and cumene hydroperoxide, and the like. Polymerization accelerators may be used in combination with the peroxide so that the monomer will rapidly polymerize at room temperature. Tertiary amines are used as polymerization accelerators, and these include, for example, include triethanol amine, N,N,3,5-tetramethyl aniline, 4-(dimethylamino)-phenethyl alcohol, dimethyl aminobenzoic acid ester, dimethyl-p-toluidine, dihydroxyethyl-p-toluidine, hydroxyethyl-p-toluidine, and the like. In addition, the catalyst paste may contain conventional polymerization inhibitors such as butylated hydroxytoluene.

Silicon dioxide, glass, titanium dioxide, iron oxide pigments, and other suitable filler materials can be added to the catalyst paste. The fillers can serve as thickening agents to provide a desired level of viscosity and/or thixotropy to the composition. Preferably, the silicon dioxide particles are in the form of silanated fumed silica. In addition, the glass filler, fluoridated barium boron alumina silicate, can be added to the paste. Significantly, the fluoridated barium boron alumina silicate glass filler is non-silanated. Because the glass filler is non-silanated, it will not bond to the polymer matrix of the paste as effectively as silanated glass fillers. The amount of bonding between the glass filler and polymer matrix is reduced. This helps to provide the final spacer material with relatively less compression strength. The spacer material will be more flexible. As a result, the spacer material will form a "temporary bond" between the "preliminary" crown and the dental tissue. As described in further detail below, a dentist can break this temporary bond easily with a probe, explorer, or other conventional instrument and remove the preliminary crown so that the final crown may be prepared and mounted on the tooth. It is recognized that a small amount of silanated glass also can be added to the catalyst paste if desired.

The catalyst paste also can include additives to provide the dental cement composition with desired properties. For example, antimicrobial agents can be added to the catalyst paste.

Base Paste for Spacer Material (Flexible Cement)

Preferably, the base paste used to form the spacer material composition comprises a polymerizable monomer, a polymerization accelerator, a polymerization inhibitor, a non-polymerizable plasticizer, and filler.

The base paste preferably contains the polymerizable monomers, urethane dimethacrylate (UDMA) and polyether diurethane methacrylate (PDM). The UDMA resin has a relatively high compressive strength. The PDM resin provides the dental cement with elastomeric properties. The PDM resin has a low viscosity (7,000-12,000 cps) and a low modulus in the cured state. The blend of UDMA and PDM resins provides a flexible cement having a relatively low compression strength and modulus. The resulting cement will not form a permanent bond between the tooth and preliminary crown.

The base paste may contain conventional polymerization accelerators such as tertiary amines including dihydroxyethyl-p-toluidine. The polymerization accelerators are used with the polymerizable initiator to increase the polymerization rate of the monomers. The base paste may also contain the same polymerization inhibitors, which are used in the catalyst paste, as described above.

The base paste may further include a non-polymerizable plasticizer such as benzyl 3-isobutryloxy-1-isopropyl-2,2-dimethylpropyl phthalate. The use of the plasticizer in base paste helps to reduce the compression strength of the cement, because it is inert to the cross-linking that occurs during polymerization. The plasticizer also serves as a carrier for the BPO which is present in the catalyst paste.

The base paste may also contain the same fillers and additives, which are used in the catalyst paste, as described above.

Alternatively, different fillers and additives can be used in the base paste than in the catalyst paste. A conventional photoinitiator is added to either the catalyst paste or base paste to make the flexible cement light-curable. Camphorquinone is typically used as a photoinitiator.

The catalyst and base pastes can be mixed together using a double barrel syringe or other suitable auto-mix system as described above. Then, the dentist applies the flexible cement to the surface of the tooth, which is being repaired, with care and precision so that no cement material is applied to the margins. Next, the dentist light-cures the cement material using a standard light-curing lamp.

After the dentist has completed the light-curing step, he or she dispenses a composite material into the previously made dental impression (transparent silicone matrix), which is described above, to make the crown. In the present invention, the composition used to form the crown also is preferably made from a base paste and catalyst paste.

Base Paste for Composite Crown-Forming Material

The base paste, which is mixed with the catalyst paste to form the composite crown material of this invention, may comprise a blend of polymerizable compound, polymerization accelerator, and filler material.

The polymerizable compound, which is used in the base and catalyst pastes, is capable of being hardened to form a polymer network. The polymerizable compound has sufficient strength and hydrolytic stability with low toxicity so that it can be used in the oral cavity.

One class of suitable polymerizable compounds contains materials having free radically active functional groups and includes monomers, oligomers, and polymers having one or more ethylenically unsaturated groups. Such free radically polymerizable compounds include, but are not limited to, mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,6-hexanediol di(meth)acrylate, pentaerythritol triacrylate, pentaerythritol tetraacrylate, pentaerythritol tetramethacrylate, sorbitol hexacrylate, 2,2-bis[4-(2-hydroxy-3-acryloyloxypropoxy)phenyl]propane; 2,2-bis[4-(2-hydroxy-3-methacryloyloxypropoxy)phenyl]propane (Bis-GMA); 2,2-bis[4-(acryloyloxy-ethoxy)phenyl]propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA); polyurethane dimethacrylate (PUDMA); alkoxylated pentacrythritol tetraacrylatel; polycarbonate dimethacrylate (PCDMA); the bis-acrylates and bis-methacrylates of polyethylene glycols; copolymerizable mixtures of acrylated monomers; acrylated oligomers; acidic monomers such as dipentaerythritol pentacrylate phosphoric acid ester (PENTA); bis[2-(methacryloxyloxy)-ethyl]phosphate; and vinyl compounds such as styrene, diallyl phthalate, divinyl succinate, divinyl adipate and divinylphthalate. The polymerizable compound can be used alone or mixtures of the polymerizable compounds can be used in the base and catalyst pastes.

Another class of polymerizable compounds that can be used in the base and catalyst paste contains materials having cationically active functional groups. This class includes, but is not limited to, cationically polymerizable epoxy resins, siloranes (compounds containing Si and O atoms in the rings), vinyl ethers, and the like.

In addition to the foregoing polymerizable compounds, the base and catalyst pastes may contain diluent, polymerizable monomers, for example, hydroxy alkyl methacrylates, ethylene glycol methacrylates, and diol methacrylates such as tri(ethylene glycol) dimethacrylate (TEGDMA) to reduce viscosity of the composition and make the composition more suitable for application.

The base paste further includes a polymerization accelerator, which is preferably a tertiary amine. Examples of tertiary amines, which can be used in the base paste include N-methyl-diethanolamine; ethyl 4-(dimethylamino)benzoate (EDMAB); 2-[4-(dimethylamino)phenyl] ethanol; N,N-dimethyl-p-toluidine (DMPT); dihydroxyethyl-p-toluidine (DHEPT); bis(hydroxyethyl)-p-toluidine; triethanolamine; and the like. A preferred polymerization accelerator is dihydroxyethyl-p-toluidine (DHEPT). The polymerization accelerators are typically present in the composition in the range of about 0.01 to about 10 wt. % based on total weight of the composition and preferably in the range of about 0.1 to about 5 wt. %. Additionally, metal ions can be used to improve the efficiency of the catalyst system. Such compounds include, but are not limited to, copper, iron, manganese, and borates.

In addition, the base paste may include a polymerization inhibitor such as, for example, butylated hydroxytoluene (BHT); hydroquinone; hydroquinone monomethyl ether; benzoquinone; chloranil; phenol; butyl hydroxyanaline (BHT); tertiary butyl hydroquinone (TBHQ); tocopherol (Vitamin E); and the like. Preferably, butylated hydroxytoluene (BHT) is used as the polymerization inhibitor. The polymerization inhibitors act as scavengers to trap free radicals in the resulting composition and to extend the working and setting time of the composition. The polymerization inhibitors are typically present in the composition in the range of about 0.01 to about 2 wt. % based on total weight of the composition. The base paste can include one or more polymerization inhibitors.

Conventional filler materials, including reactive and non-reactive fillers, may be added to the base and catalyst pastes. Reactive fillers include metal oxides and hydroxides, metal salts, and glasses that are acid-reactive. Such fillers are commonly used in dental ionomer cements. Examples of metal oxides include, but are not limited to, barium oxide, calcium oxide, magnesium oxide, and zinc oxide can be used. Examples of metal salts include, but are not limited to, aluminum acetate, aluminum chloride, calcium chloride, magnesium chloride, zinc chloride, aluminum nitrate, barium nitrate, calcium nitrate, magnesium nitrate, and strontium nitrate. Suitable glasses include, but are not limited to, borate glasses, phosphate glasses, and fluoroaluminate glasses. The glasses may or may not have fluoride-releasing properties. The benefits of using fluoride-releasing glasses are well known. Such materials are capable of releasing fluoride into the oral cavity over the long term. Fluoride generally provides added protection against acid attack that can cause tooth decay. Although, such fluoride-releasing glasses are generally not used in temporary dental restorations, since such restorations are intended for short-term use only. Mixtures of the above-described filler materials also can be used in the base and catalyst pastes if desired.

It further is recognized that a wide variety of non-acid reactive filler materials can be added to the base and catalyst pastes. Inorganic fillers, which can be naturally-occurring or synthetic, can be added. Such materials include, but are not limited to, silica, titanium dioxide, iron oxides, silicon nitrides, glasses such as calcium, lead, lithium, cerium, tin, zirconium, strontium, barium, and aluminum-based glasses, borosilicate glasses, strontium borosilicate, barium silicate, lithium silicate, lithium alumina silicate, kaolin, quartz, and talc. Preferably, the silica is in the form of silanized fumed silica. A preferred glass filler is silanized barium boron aluminosilicate. Organic particles such as polycarbonates and polyepoxides also can be used as fillers if desired. Furthermore, unconventional filler materials including, but not limited to, liquid crystalline polymers (LCPs), partially polymerized polymers (nanogels), and fibers (e.g., glass, carbon, or high-strength synthetic fibers) could be used in the composition of this invention.

The average particle size of the particles comprising the filler material is normally in the range of about 0.1 to about 10 microns and more preferably in the range of about 0.1 to about 5 microns. If a fumed silica filler material is used, the silica particles are preferably nanometer-sized. The silica particles preferably have an average diameter of less than 200 nm. The filler particles can be surface-treated with a silane compound or other coupling agent to improve bonding between the particles and resin matrix. Suitable silane compounds include, but are not limited to, gamma-methacryloxypropyl-trimethoxysilane, gamma-mercaptopropyltriethoxysilane, gamma-aminopropyltrimethoxysilane, and combinations thereof.

The base paste may further include a non-polymerizable plasticizer including, but not limited to, diethyl phthalate (DEP), dibutyl phthalate (DBP), low-molecular weight polyglycols, polyesters, polypropylene oxide monomethacrylate, and the like. The plasticizer is generally present in an amount in the range of about 1 to about 20% by weight.

The base paste also can include additives to provide the composition with specially desired properties. For example, antimicrobial agents including, but not limited to, 2,4,4-trichloro-2-hydroxy-diphenyl ether (TRICLOSAN), chlorhexidine compounds, hexetidine, alexidine, quaternary ammonium antimicrobial compounds and metal-ion containing antimicrobial compounds; fluoride-releasing agents; flavorants; pigments; fluorescent agents; opalescent agents; ultra-violet stabilizers; anti-oxidants; viscosity modifiers, and the like can be added to the base paste.

Catalyst Paste for Composite Crown Material

Preferably, the catalyst paste used to form the composite crown-forming material comprises a blend of polymerizable compound; polymerization initiator, and filler material.

The polymerizable compounds, which are useful for adding to the base paste, also may be used in the catalyst paste; provided however, that the base and catalyst pastes contain at least one different polymerizable compound. Suitable polymerizable compounds that can be used in the catalyst paste are described above. Such compounds include, but are not limited to, 2,2-bis[4-(2-hydroxy-3-methacryloyloxypropoxy)phenyl]propane (Bis-GMA); 2,2-bis[4-(acryloyloxyethoxy)phenyl]propane; 2,2-bis[4-(methacryloyloxyethoxy)phenyl]propane (or ethoxylated bisphenol A-dimethacrylate) (EBPADMA); urethane di(meth)acrylate (UDMA); diurethane dimethacrylate (DUDMA); polyurethane dimethacrylate (PUDMA); and the like. The polymerizable compounds can be used alone in the catalyst paste or mixtures of the polymerizable compounds can be used.

The catalyst paste also may contain diluent monomers, which are used in the base paste, as discussed above. Suitable diluent monomers include, but are not limited to, hydroxy alkyl methacrylates, ethylene glycol methacrylates, and diol methacrylates. Preferably, the catalyst paste contains tri(ethylene glycol) dimethacrylate (TEGDMA).

In one embodiment, the catalyst paste comprises a blend of 2,2-bis[4-(2-hydroxy-3-methacryloyloxypropoxy)phenyl] propane (Bis-GMA); ethoxylated bisphenol A-dimethacrylate (EBPADMA); and tri(ethylene glycol) dimethacrylate (TEGDMA). The polymerizable compounds are typically present in the catalyst paste in an amount in the range of about 10% to about 90% based on the total weight of the catalyst paste and preferably in an amount in the range of about 20% to about 70%.

Polymerization initiators, such as peroxides, are preferably added to the catalyst paste to make the composition self-curable. The peroxides in the catalyst paste generate free radicals to initiate polymerization and hardening of the composition at room temperature. Peroxides such as dibenzoyl peroxide (BPO), di-p-chlorobenzoyl peroxide, di-2,4-dichlorobenzoyl peroxide, tertiary butyl peroxybenzoate, methyl ethyl ketone peroxide, ditertiary butyl peroxide, dicumyl peroxide and cumene hydroperoxide, and the like can be added to the catalyst paste.

In addition, the catalyst paste may include a polymerization inhibitor, which also is used in the base paste, as discussed above. Suitable polymerization inhibitors include, for example, butylated hydroxytoluene (BHT); hydroquinone; hydroquinone monomethyl ether; benzoquinone; chloranil; phenol; butyl hydroxyanalin (BHT); tertiary butyl hydroquinone (TBHQ); tocopherol (Vitamin E); and the like. Preferably, the same inhibitor, butylated hydroxytoluene (BHT), which is used in the base paste, is used also in the catalyst paste. The catalyst paste can include one or more polymerization inhibitors.

The catalyst paste may contain fillers and additives selected from the same group of fillers and additives used in the base paste as described above. The catalyst and base pastes may include the same fillers. For example, the base paste may include a mixture of silanated barium boron aluminosilicate glass filler and fumed silica. Alternatively, the catalyst paste may contain different fillers.

Additives such as, for example, antimicrobial agents; fluoride-releasing agents; flavorants; pigments; fluorescent agents; opalescent agents; ultra-violet stabilizers; anti-oxidants; viscosity modifiers, and the like can be added to the catalyst paste to impart desired properties to the composition.

A photoactive agent such as, for example, benzophenone, benzoin and their derivatives, or alpha-diketones and their derivatives is added to the base or catalyst paste in order to make the composite material light-curable. A preferred photopolymerization initiator is camphorquinone (CQ). Photopolymerization can be initiated by irradiating the composition with blue, visible light preferably having a wavelength in the range of about 400 to about 500 nm. A standard dental blue light-curing unit can be used to irradiate the composition. The camphorquinone (CQ) compounds have a light absorbency maximum of between about 400 to about 500 nm and generate free radicals for polymerization when irradiated with light having a wavelength in this range. Alternatively, the photoinitiator can be selected from the class of acylphosphine oxides such as monoacyl phosphine oxide derivatives, bisacyl phosphine oxide derivatives, and triacyl phosphine oxide derivatives. For, example, 2,4,6-trimethylbenzoyl-diphenyl-phosphine oxide (TPO) can be used as the photopolymerization initiator.

The base and catalyst pastes are preferably mixed together and dispensed using an auto-mix system as described above. As the amine-containing base paste and peroxide-containing catalyst paste are extruded through the static mixer in the auto-mix system, they are combined and mixed together. Photopolymerization is initiated by irradiating the composition with blue, visible light preferably having a wavelength in the range of about 400 to about 500 nm.

In the method of this invention, the dentist places layers of the composite crown-forming material into the impression of the tooth, which will receive the crown, beginning with the enamel layer. As the dentist applies the enamel layer, he or she carefully thins out the areas around the margins with a brush. Then, the dentist applies more composite material to form the dentin layer making sure that the correct amount of composite material is placed in the impression. If a sufficient amount of composite material is not introduced, gaps will form in the resulting crown, and there will be occlusion problems. On the other hand, if too much composite material is introduced, there also may be occlusion problems with the resulting crown. In such instances, the occlusion of the crown may be too high. The dentist may carefully customize the shade of the composite material so that it matches the color of the patient's natural teeth.

The dentist then inserts the silicone matrix, containing the composite crown-forming material, into the patient's mouth. The composite material is molded over the prepared tooth so that it forms a crown for the tooth. Then, the shaped composite material is light-cured. A standard light-curing dental lamp may be used to cure the composite. Since the matrix containing the composite material is transparent, the curing light is able to pass through the matrix and cure the composite. As photopolymerization of the composition is initiated, the composition hardens and cures into a dental crown.

Next, the dentist removes the crown from the tooth. The dentist may use an explorer, probe, crown remover, or other suitable instrument to detach the crown. Under ordinary circumstances, the dentist would have difficulty removing the crown from the tooth. However, because a flexible spacer material is used in accordance with this invention, the dentist is able to remove the crown easily from the tooth. The flexible spacer material is formulated so that it does not strongly adhere to the surface of the tooth. Thus, the surface of the tooth is left relatively clean after the crown has been removed. However, the flexible cement does adhere strongly to the inner surface of the crown.

After removing the crown, the dentist may observe some residual cement located on the inner surface of the crown because of the strong adherence of the flexible cement. The dentist can easily remove this cement with a curette or similar instrument to generate a clean inner surface. Now, the crown is ready to be permanently affixed to the tooth. The crown can be finished with burs and polished using customary crown-finishing methods if the dentist believes these steps are necessary. A sealant, which provides a stain-resistant and glossy surface finish may be applied to the crown. Then, the finished crown is permanently affixed to the tooth using a permanent cement. Conventional permanent cements, as known in the dental industry, may be used in this step. The dental crown made in accordance with the method of this invention has good mechanical strength and is resistant to fracturing and breaking.

What is claimed is:

1. A method of forming a permanent dental crown, comprising in sequence the steps of:
   providing a polymerizable flexible cement composition comprising a blend of urethane dimethacrylate and polyether diurethane methacrylate;
   applying the cement composition to a prepared tooth surface and polymerizing the composition so that it substantially hardens and forms a flexible spacer material;

dispensing a composite crown-forming material into a substantially transparent plastic matrix, the composite material having a polymerization system capable of being activated by light;

placing the plastic matrix in a mouth of a patient so that the composite material is molded over the tooth surface;

irradiating the composite material in the plastic matrix with light so that the material polymerizes and hardens to form a crown;

removing the hardened crown from the surface of the tooth; and permanently affixing the crown to the tooth using permanent dental cement.

2. The method of claim 1, wherein the cement composition is light curable.

3. The method of claim 1, wherein the composite crown-forming material is prepared from a base and catalyst paste.

4. The method of claim 1, wherein the composite crown-forming material comprises a photopolymerization initiator.

5. The method of claimed 1, wherein the photopolymerization initiator is camphorquinone (CQ).

6. The method of claim 1, wherein the composite material is irradiated with blue, visible light having a wavelength in the range of about 400 to about 500 nm.

7. The method of claim 1, wherein the hardened crown is trimmed and shaped after removing the crown from the surface of the tooth and prior to permanently affixing the crown on the tooth.

8. The method of claim 7, wherein a sealant is applied to the hardened crown after the crown has been trimmed and shaped.

* * * * *